United States Patent
Yamane et al.

(10) Patent No.: US 7,145,595 B2
(45) Date of Patent: Dec. 5, 2006

(54) IMAGE PROCESSING AND INSPECTION SYSTEM

(75) Inventors: Toshiki Yamane, Sakai (JP); Masayuki Hattori, Kyoutanabe (JP); Jun Nishijima, Katono (JP); Osamu Iijima, Itabashi-ku (JP); Yoshinori Koizumi, Yokohama (JP)

(73) Assignee: Matsushita Electric Works, Ltd., Kadoma (JP)

( * ) Notice: Subject to any disclaimer, the term of this patent is extended or adjusted under 35 U.S.C. 154(b) by 583 days.

(21) Appl. No.: 10/399,869

(22) PCT Filed: Aug. 28, 2002

(86) PCT No.: PCT/JP02/08691

§ 371 (c)(1),
(2), (4) Date: Apr. 29, 2003

(87) PCT Pub. No.: WO03/019162

PCT Pub. Date: Mar. 6, 2003

(65) Prior Publication Data

US 2004/0061778 A1 Apr. 1, 2004

(30) Foreign Application Priority Data

Aug. 31, 2001 (JP) .......................... 2001-264782

(51) Int. Cl.
*H04N 7/18* (2006.01)
(52) U.S. Cl. ......................................... 348/92; 348/94
(58) Field of Classification Search ............. 348/80–98
See application file for complete search history.

(56) References Cited

U.S. PATENT DOCUMENTS

| 4,570,180 | A | | 2/1986 | Baier et al. | |
|---|---|---|---|---|---|
| 6,151,064 | A | * | 11/2000 | Connolly et al. | 348/93 |
| 6,415,191 | B1 | * | 7/2002 | Pryor | 700/95 |
| 6,442,291 | B1 | * | 8/2002 | Whitman | 382/141 |
| 6,741,275 | B1 | * | 5/2004 | Frigon et al. | 348/91 |
| 2001/0022614 | A1 | * | 9/2001 | Iida et al. | 348/92 |

FOREIGN PATENT DOCUMENTS

| JP | 07 210657 | 8/1995 |
|---|---|---|
| JP | 11 066281 | 3/1999 |
| WO | 99 63484 | 12/1999 |

* cited by examiner

*Primary Examiner*—Andy Rao
(74) *Attorney, Agent, or Firm*—Oblon, Spivak, McClelland, Maier & Neustadt, P.C.

(57) ABSTRACT

An image processing and inspection system includes a master device (10) having a video camera (40) and a first controller (20) responsible for processing and inspecting the image of an object (1) in accordance with inspection criteria. Intercommunicated (12) with the master device (10) is a personal computer (100) equipped with a second monitor (120), and a second input member (102,104). The motion-picture taken by the camera (40) for inspection on the side of the master device (10) is transmitted to the computer (100) so as to be displayed on the second monitor (120) as a real-time image of the object (1) for easy confirmation of the object on the side of the computer (100), thereby enabling to determine the inspection criteria on the side of the computer (100) while monitoring the real-time image of the object (1).

22 Claims, 9 Drawing Sheets

IMAGE PROCESSING AND INSPECTION SYSTEM

TECHNICAL FIELD

The present invention is directed to an image processing and inspection system adapted for use in a production line to analyze the quality of an object in accordance with predetermined inspection criteria.

BACKGROUND ART

An image processing and inspection system has been widely utilized by many industrial users for testing objects running in a production line in accordance with predetermined inspection criteria with regard to, for example, dimensions, colors, and contours in a target area of the object. The system utilizes a video camera taking a motion-picture image of the object, a monitor displaying the motion-picture image, an input instrument for entry of parameters determining the inspection criteria, and a dedicated controller which executes an inspection program to inspect the object in accordance with the inspection criteria. The controller runs on a particular operation system which is normally compact for sake of simplicity and cost-effectiveness to provide only a minimum visual information on the monitor with regard to the entry of various parameters determining the criteria. In the meanwhile, a computer technology is ever developing to give an enhanced GUI (graphical user interface) providing versatile visual information easy to be interact with by use of a pointing device and a menu provided by the visual information. Accordingly, it has been desired to combine a computer having the GUI with the device for inspection of the object. In this connection, Japanese Patent Publication No. 7-210657 discloses a typical prior image processing and inspection system composed of a master device responsible for inspection of the object and a remote computer which is intercommunicated through a transmission line with the master device. The computer includes a keyboard and a monitor and is configured to provide the menu by taking an advantage of the GUI for entry of the parameters determining the inspection criteria, thereby simplifying the determination of the inspection criteria rather than resorting to the awkward input instrument on the side of the master device. However, due to insufficient capability which the master device has in transmitting vast data of the current motion-picture image to the computer, it has been a practice to rely upon the monitor of the master device when determining the inspection criteria by use of the keyboard on the side of the computer. Therefore, the computer has to be positioned close to the master device at least initially for setting the criteria, which detracts from the way in which the computer is capable of being located remote from the master device.

DISCLOSURE OF THE INVENTION

In order to overcome the above insufficiency and inconvenience, the present invention has been accomplished to provide an improved image processing and inspection system which enables to give inspection criteria by taking an advantage of a computer incorporated in the system. The system includes a master device and the computer which are linked for intercommunication with each other. The master device is adapted to be located in the vicinity of the object to be responsible for inspection of the object, and includes a video camera taking a motion-picture image as a sequence of still-picture images of the object, a first monitor, and a first controller which is programmed to display on the first monitor the motion-picture image as well as a menu prompting an entry of inspection criteria. Also included in the master device is a first input means for inputting the inspection criteria. The first controller operates to process and inspect the still-picture image in accordance with the inspection criteria to give inspection results with regard to the object, and to transmit at least one of the inspection results and the still-picture image to the computer. On the other hand, the computer is adapted to be installed in a location remote from the master device and includes a second monitor, a second controller which is programmed to display on the second monitor a menu prompting an entry of the inspection criteria, and to display the inspection results together with the still-picture image on the second monitor. A second input means is included in the computer for entering the inspection criteria separately from the first input means. The second controller operates to transmit the inspection criteria entered at the second input means to the first controller for inspection of the still-picture image at the first controller in accordance with the inspection criteria thus transmitted. The important feature of the present system resides in that the first controller transmits the instant motion-picture image to the computer, and that the second controller displays the instant motion-picture image on the second monitor. Accordingly, the system of the present invention enables to determine the inspection criteria while monitoring instant motion-picture image on the side of the computer at a location remote from the object. Thus, it is possible to take an advantage of a graphical user interface that the computer is inherently given for simplifying the setting of the inspection criteria, which is a primary object of the present invention.

Preferably, the first controller provides in the menu on the first monitor an operation mode of determining which one or both of the master device and the computer is responsible to give the inspection criteria for the inspection of the object at the first controller. Also, the second controller provides in the menu on the second monitor an operation mode of determining which one or both of the master device and the computer is responsible to give the inspection criteria for the inspection of the object at the first controller. Thus, the system can be easily streamlined to match with a preference of an operator.

Also, the system may be configured such that the first controller provides in the menu on the first monitor a display mode of determining which one or both of said first monitor and said second monitor is enabled, and that the second controller provides in the menu on the second monitor a display mode of determining which one or both of the first monitor and the second monitor is enabled. In this sense, the system can be further streamlined in match with the operator's preference.

The second controller may be designed to provide in the menu on the second monitor an fps mode of designating an fps value which is the number of frames being transferred of the motion-picture image being transferred per second from the master device to the computer. The designated fps value is sent to the first controller which responds to transfer the motion-picture image at the designed fps value. Accordingly, the operator on the side of the computer can suitably select the speed at which the motion-picture image is reproduced on the second monitor for balancing the speed and a traffic load in the communication link between the master device and the computer.

Further, the second controller is preferred to monitor a data transmission speed at which the motion-picture image is being sent from th master device, and send the monitored data transmission speed to the first controller so that the first controller can make data compression of the motion-picture image in response to the data transmission speed lowering from a critical level. Thus, even when the data transmission speed is lowered accidentally by some reasons, the current motion-picture image can be successfully reproduced on the side of the computer, assuring the determination of the inspection criteria on the side of the computer by referring to the current motion-picture image. Preferably, the data compression may be made by a lossy compression technique of eliminating fractions of pixels of the motion-picture image.

Alternatively, the first controller may be configured to reduce a number of frames of the motion-picture image being transmitted per unit time as the transmission speed becomes lower than the critical level, assuring to rely on the motion-picture image in determination of the inspection criteria on the side of the computer even in a condition where the data transmission speed becomes lowered.

Further, in order to reduce a load in transmitting the motion-picture image to the computer as well as to effectively select the target area of the image to be inspected, the second controller of the computer is configured to provide in the menu on the second monitor a trim mode for cutting the motion-picture image into a segment of a desired size, and to transmit a trimming instruction with information of the size of the segment when the motion-picture image is cut into the segment. In response to the trimming instruction, the first controller operates to transmit the segmented motion-picture image to the computer. Accordingly, it is possible to reduce the amount of the data transmission so as to keep transmitting the motion-picture image in a real-time fashion from the master device to the computer even at the lowered data transmission speed, while limiting the motion-picture image only to the target area to be inspected.

The second controller is preferably designed to provide in the menu on the second monitor a parameter import-export mode for taking from the first controller the parameters determining the inspection criteria as well as sending to the first controller the parameters entered on the side of the computer for determination of the inspection criteria. The parameters are stored in memories respectively included in the first and second controllers. Thus, the inspection criteria can be exchanged in this manner between the master device and the computer, so that the inspection criteria can be modified at either one of the master device and the computer to enhance operability of the system.

The memory of the first controller is utilized to store an inspection program describing a sequence of inspecting the object. Also included in the menu on the second monitor is a programming mode for enabling the computer to make the inspection program by its own and store the program in a memory of the computer. The second controller provides in the menu on the second monitor a program import-export mode for taking the inspection program from the memory of the master device for revising it on the side of the computer as well as sending to the master device the inspection program stored in the memory of the computer. Accordingly, the inspection program running on the master device can be easily modified or replaced with a new one written on the side of the computer by taking an advantage of enhanced writing capability given to the computer.

Still further, the inspection results are stored in the memory of the second controller together with the associated still-picture image transmitted from the master device. The second controller is designed to provide in the menu on the second monitor an export mode for transmitting to the first controller the still-picture image as well as modified inspection criteria entered at the second input means and requesting another inspection of the still-picture image based upon the modified inspection criteria. Thus, it is easy to check how the modified inspection criteria leads to the inspection results on the same still-picture image, which is helpful for altering the inspection criteria effectively and efficiently for evaluation of the object.

The computer is preferably a personal computer equipped with a keyboard and a pointing device which defines the second input means for facilitating the entry of the inspection criteria.

These and still other objects and advantageous features of the present invention will become more apparent from the following detailed description of the preferred embodiment when taken in conjunction with the attached drawings.

BRIEF DESCRIPTION OF THE DRAWINS

DETAILED DESCRIPRION OF THE EMBODIMENT

Figure 1:
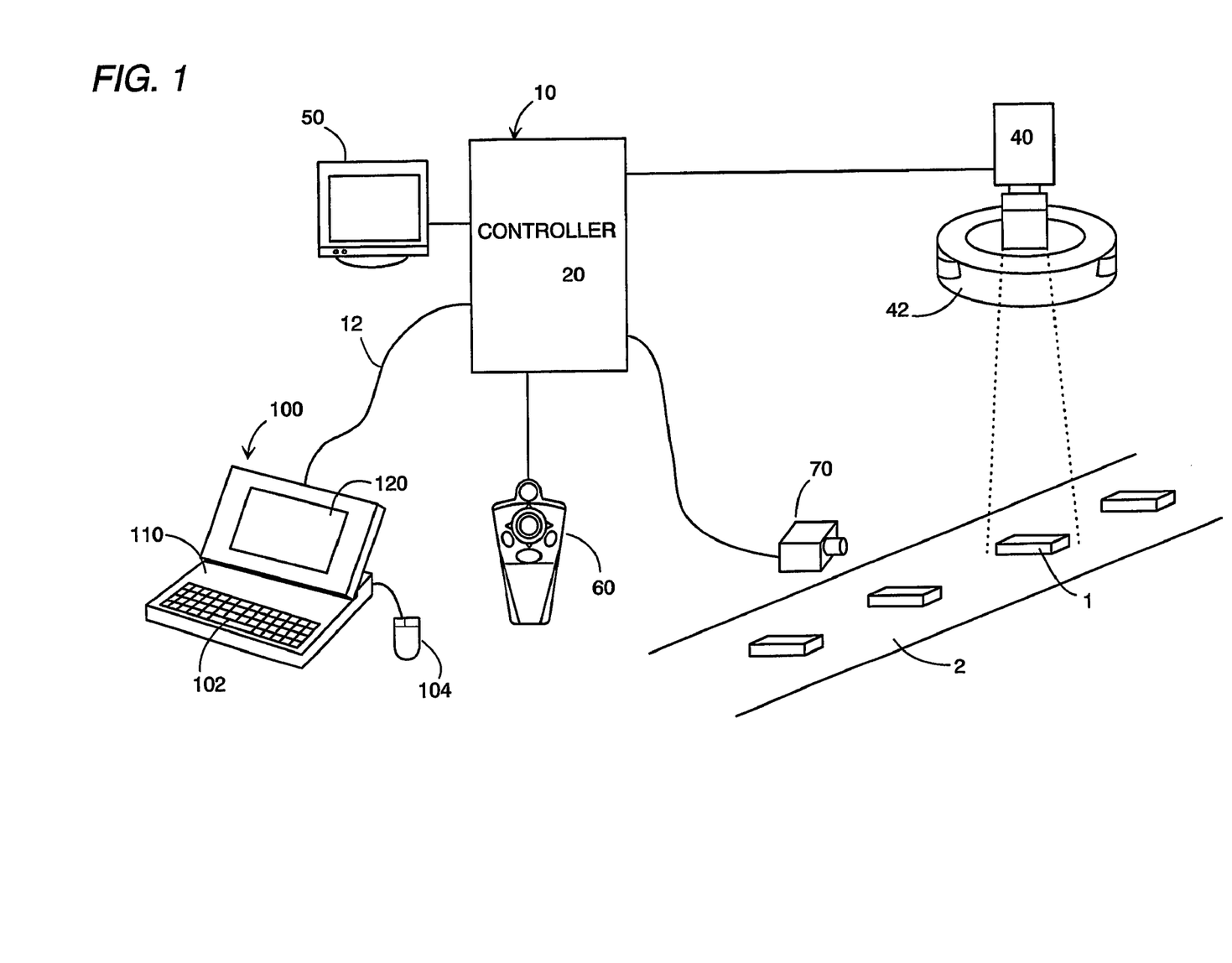
FIG. 1 is a schematic diagram illustrating an image processing and inspection system in accordance with a preferred embodiment of the present invention.

Referring now to FIG. 1, there is shown an image processing and inspection system in accordance with a preferred embodiment of the present invention. The system is utilized to test objects 1, for example, an industrial products running on a production line 2 for examining whether or not the object is acceptable in view of predetermined inspection criteria. The inspection criteria normally include dimensions, colors, and contours in a target area of the object. The system includes a master device 10 composed of a first controller 20, a video camera 40 taking a motion-picture image of the object, and a first monitor 50 displaying the motion-picture being taken as well as a menu for prompting an operator to enter various parameters or settings that determine the inspection criteria. The motion-picture is a sequence of still-picture images taken, for example, in 30 frames per second, and is sent to the first monitor 50. A key pad 60 is included in the master device 10 to select item in the menu as well as enter the parameters with reference to guide information appearing on the monitor 50. The controller 20 is connected to an object sensor 70 so as to start an inspection task by activating the camera 40 and an illuminator 42 directed to the object. The controller 20 operates to obtain a single still-picture image of the object from the motion-picture image in synchronous with the moving speed of the object for inspection. Thus obtained still-picture image is then processed to make position correction, area measurement, center of gravity calculation, etc. so that the processor inspects the image of object in accordance with the inspection criteria to give inspection results for quality evaluation of the object.

The present system further includes a computer 100 incorporating a second controller 110, a keyboard 102 and a pointing device, i.e., a mouse 104, and a monitor 120. The controller 110 is realized by a combination of hardware and an application software running on a window operating system. The controller 110 is linked by way of a communication interface (not shown) attached to the computer 100 to the master device through a communication interface 32 provided in the first controller 20. One typical example of the communication interface is IEEE1394, USB, or the like communication interface compatible with a high speed Ethernet capable of exchanging data at a transfer rate of 60 Mbps or more. The controller 110 receives at least the motion-picture image and the inspection results from the master device 10 through the communication link 12 in order to display the same on the monitor 120. For this purpose, the controller 110 is programmed to provide on the monitor 120 a motion-picture window 121 for displaying the current motion-picture image being taken by the video camera 40. It is noted that the motion-picture image is transmitted from the mater device to the computer in response to a request from the computer 100. However, the motion-picture image can be transmitted constantly to the computer. In addition, the controller 110 is designed to present on the monitor 120 a menu prompting the operator to select items and/or enter various data with the use of the keyboard 102 and the mouse 104. The keyboard and the mouse are hereinafter referred to collectively as a second input means, while the keypad 60 of the master device is referred to as a first input means. In this connection, the controller 20 of the master device 10 is hereinafter referred to as the first controller, while the controller 110 of the computer is referred to as the second controller for an easy reference purpose. Likewise, the monitor 50 of the master device 10 and the monitor 120 of the computer 100 are respectively referred to as the first monitor and the second monitor.

Figure 2:
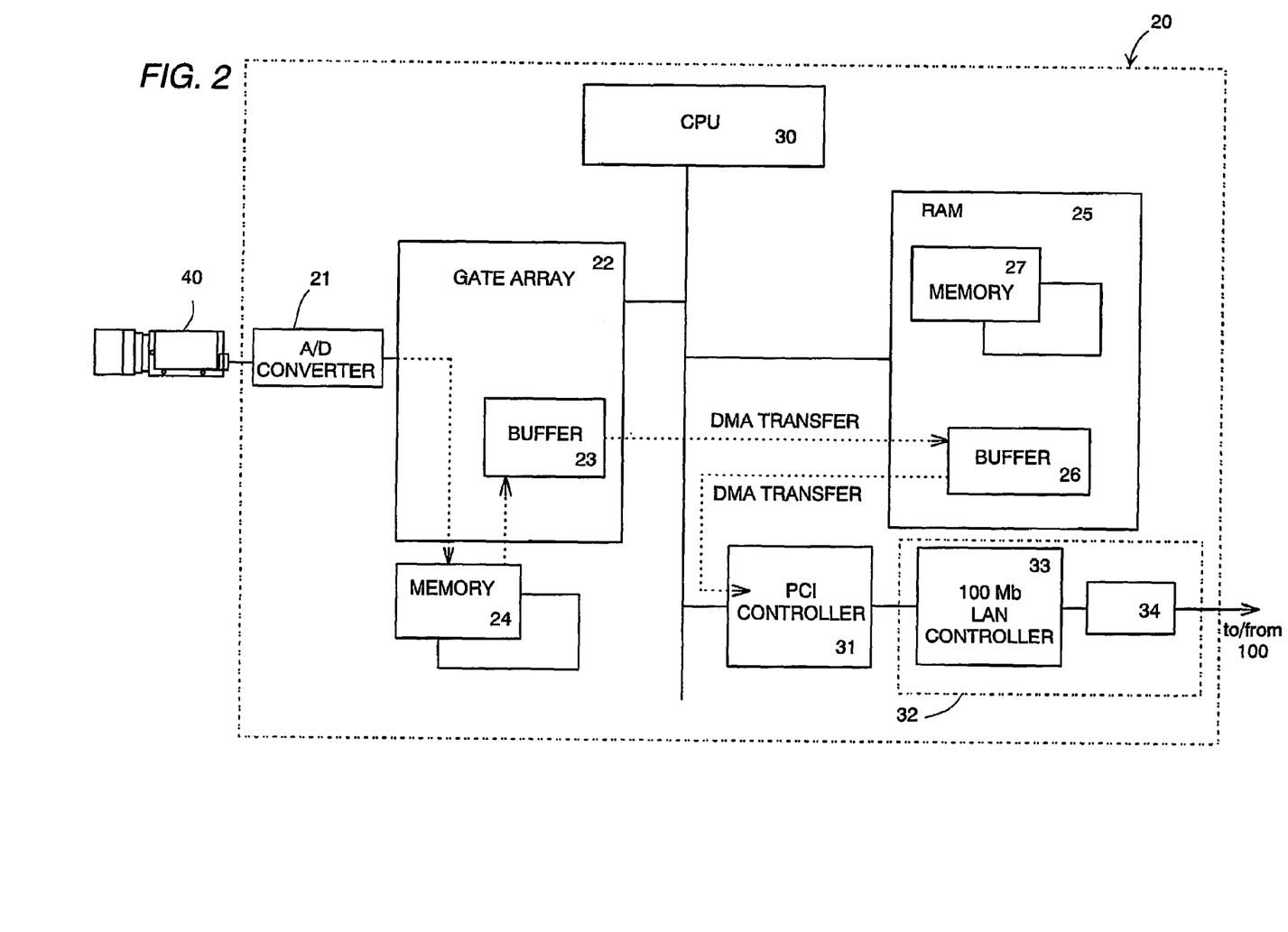
FIG. 2 is a circuit block diagram of a first controller included in a master device constituting the above system.

Referring to FIG. 2, first controller 20 is explained in detail. The image data from the video camera 40 is converted through an A/D converter 21 into a digital data which is fed by way of a gate array 22 to be stored in a memory 24. The gate array 22 is also responsible for fetching the frames, i.e., a succession of the still-picture images one by one from the memory 24 under the control of a CPU 30 and for sending by a known DMA technique the image data through a one-line buffer 23 into a one-frame buffer 26 in a RAM 25. Then, the image data of each frame is transferred line by line to the computer 100 through a PCI (peripheral Component Interconnect) controller 31 and the communication interface 32 composed of a 100 Mbs LAN controller 33 and an associate controller 34. When receiving the image data thus transferred from the master device 10 through a communication link 12, the second controller 110 of the computer responds to display the motion-picture image in the motion-picture window 121 of the second monitor 120 so that the operator on the side of the computer can monitor the real time image being taken by the camera. For example, each frame of the image has 512×480 pixels with 8 bits for each pixel and is transferred one line by one line at a transfer rate of 60 Mbs or higher so that 30 frames of the image per second can be received at the computer 100 for real-time reproduction of the motion-picture image.

Figure 3:
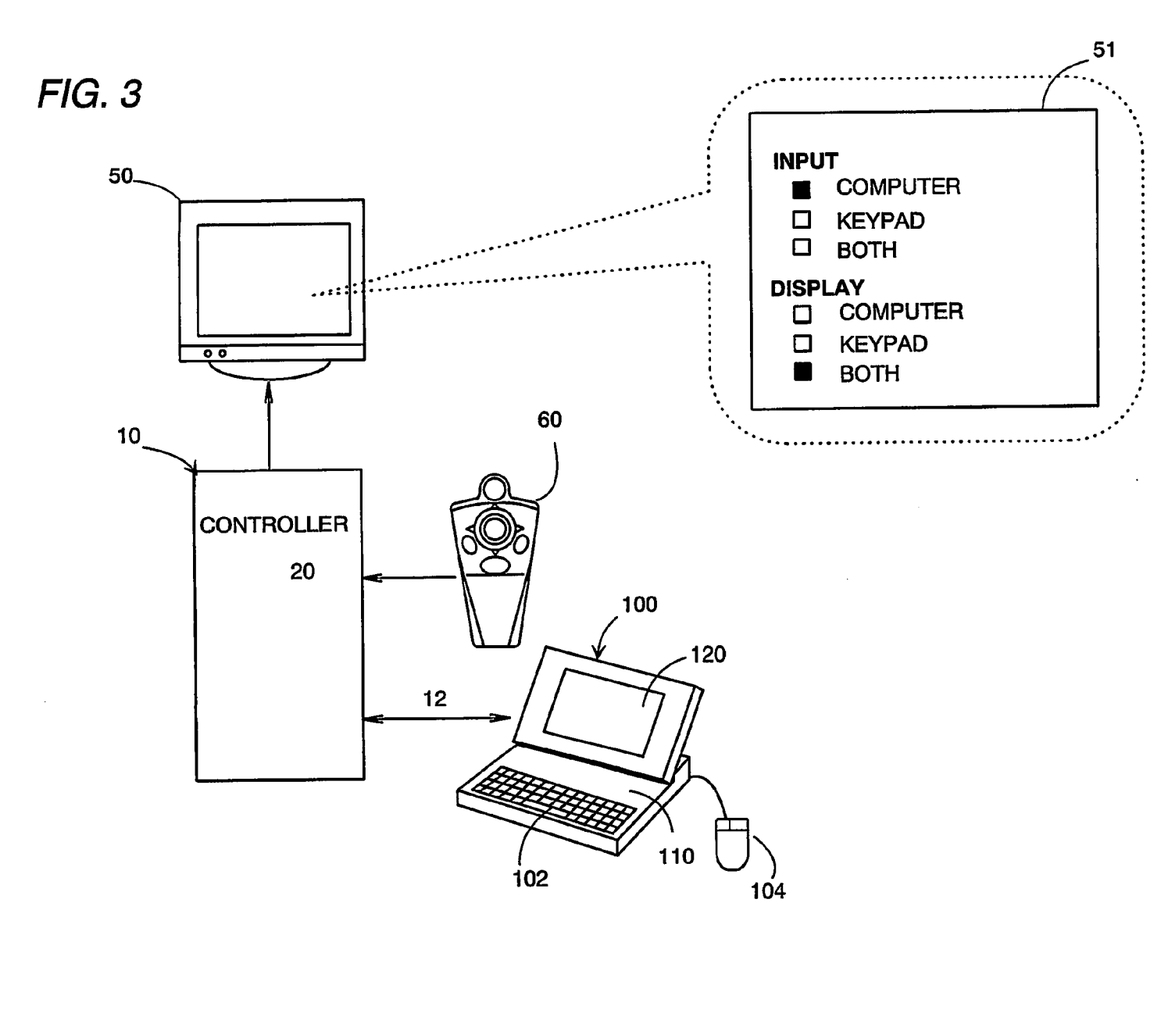
FIGS. 3 to 9 are schematic views respectively illustrating visual information presented on first and second monitors of the above system for selection by an operator.

The first controller 20 includes a memory 27 which stores an inspection program which is executed by CPU 30 for inspection of the object based upon the still-picture image selected in synchronous with the running speed of the object 1. The inspection is made in accordance with the inspection criteria determined by various parameters which are entered at either one of the first input means or the second input means, and are also stored in the memory 27. As seen in FIG. 3, the first monitor 50 gives a menu 51 for selection of operation mode and a display mode. The operation mode is given for selection by the operator using the keypad 60 which one or both of the first input means (keypad) 60 and the second input means (keyboard/mouse) 102/104 is enabled for entry of data. The display mode is given for selection which one or both of the first monitor 50 and the second monitor 120 is enabled to display necessary information including the motion-picture image. The parameters for determination of the inspection criteria entered at the second input means are transferred from the computer 100 to the first controller 20 under the control of the second controller and stored in the memory 27. The inspection results are also stored in memory 27 together with the associated still-picture image, and are displayed on the first monitor 50 when it is selected to be enabled. The inspection results and the associated still-picture image are transmitted to the computer 100 to be displayed on the second monitor 120 when it is selected to be enabled, and also be stored in a memory included in the computer 100, i.e., the second controller 110. It is noted in this connection that the first controller 20 can transmit the still-picture image that has not been inspected to the computer 100 such that fresh inspection criteria can be set on the side of the computer 100 with reference to thus transmitted still-picture image. Further, the first controller 20 can be made to transmit the inspection results not accompanied with the associated still-picture image.

Figure 4:
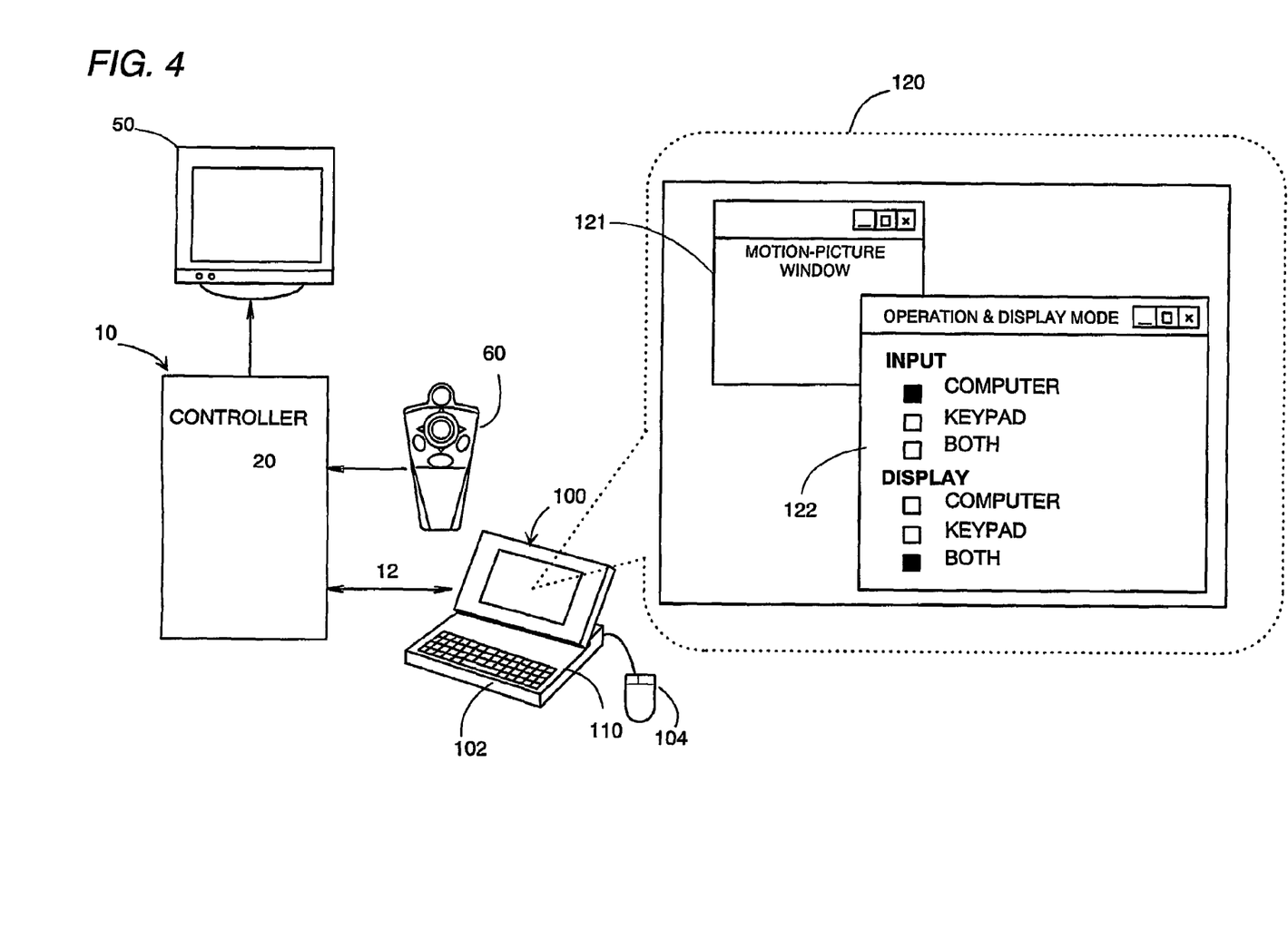

As shown in FIG. 4, the computer 100 also provides in the menu on the second monitor 120 a window 122 of selecting a operation mode and a like display mode, in addition to the motion-picture window 121. Thus, the operator can use the second input means to select which one or both of the first input means (keypad) 60 and the second input means (keyboard/mouse) 102/104 is enabled for entry of data, and which one or both of the first monitor 50 and the second monitor 120 is enabled to display necessary information including the motion-picture image. As will be discussed later, the inspection criteria utilized for inspection of the object are stored in both of the master device 10 and the computer 100 together with the still-picture image, irrespective of which one of the first and second input means is relied on to enter the data, i.e., the parameters determining the inspection criteria.

Figure 5:
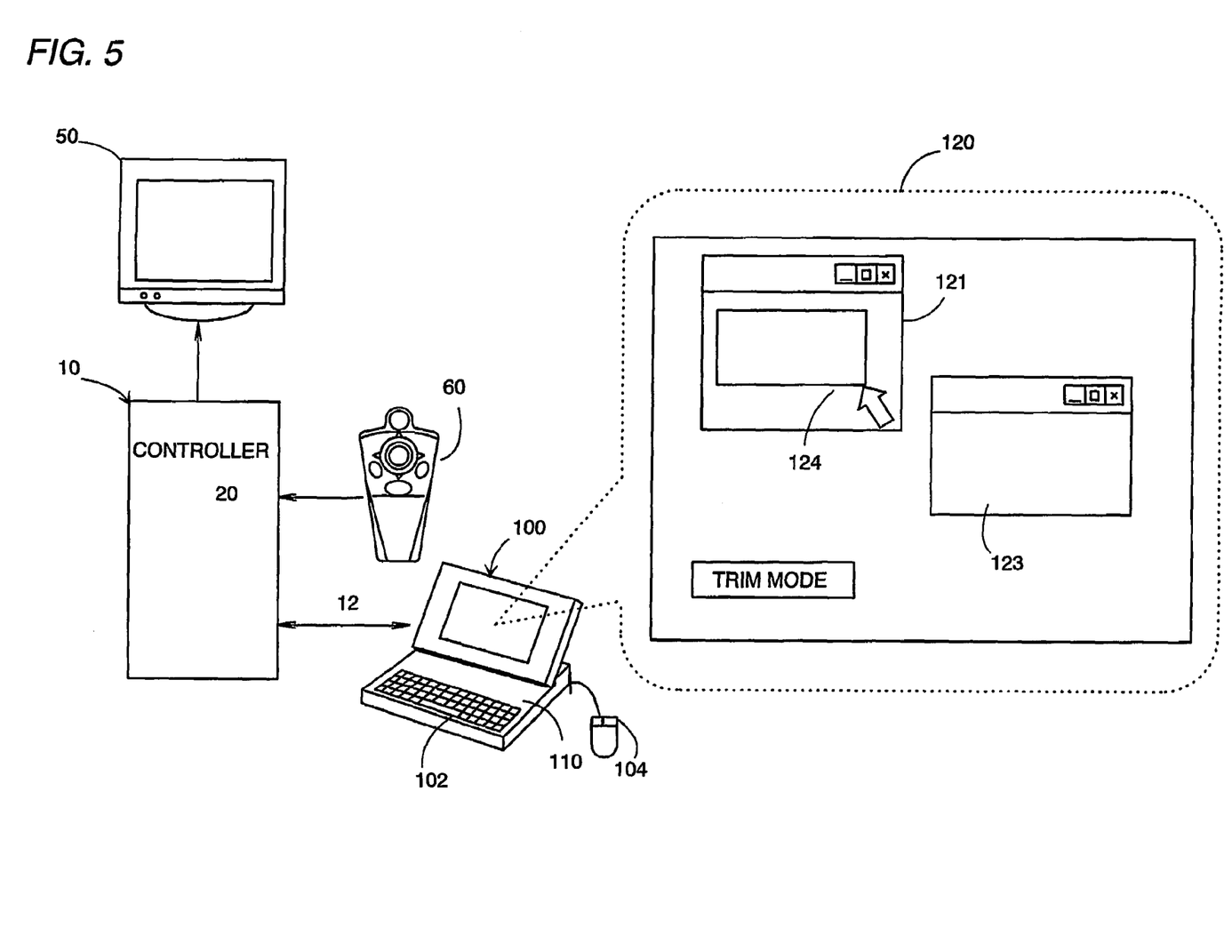

As shown in FIG. 5, included in the menu on the second monitor 120 is a trimming-window 123 which is created by the second controller 110 to give a trim mode for cutting the motion-picture image displayed in the motion-picture window 121 into a partial image or segment to be subject to the inspection. The partial image is trimmed from the original image by use of a masking rectangle 124 and appears in the trimming-window 123 for confirmation. When the image is trimmed, the second controller 110 transmits to the first controller 20 a trimming instruction accompanied with information of the size of the segment. In response to the trimming instruction, the first controller 20 acts to reduce the size and therefore the amount of the image data, and transmit the correspondingly segmented motion-picture to the computer as the real-time motion-picture image. Thereafter, thus segmented or partial motion-picture image is reproduced in the motion-picture window 121. This is advantageous not only for limiting the image to a necessary target area to be easily confirmed by the operator but also for reducing a traffic load running through the communication link to the computer 100.

Figure 6:
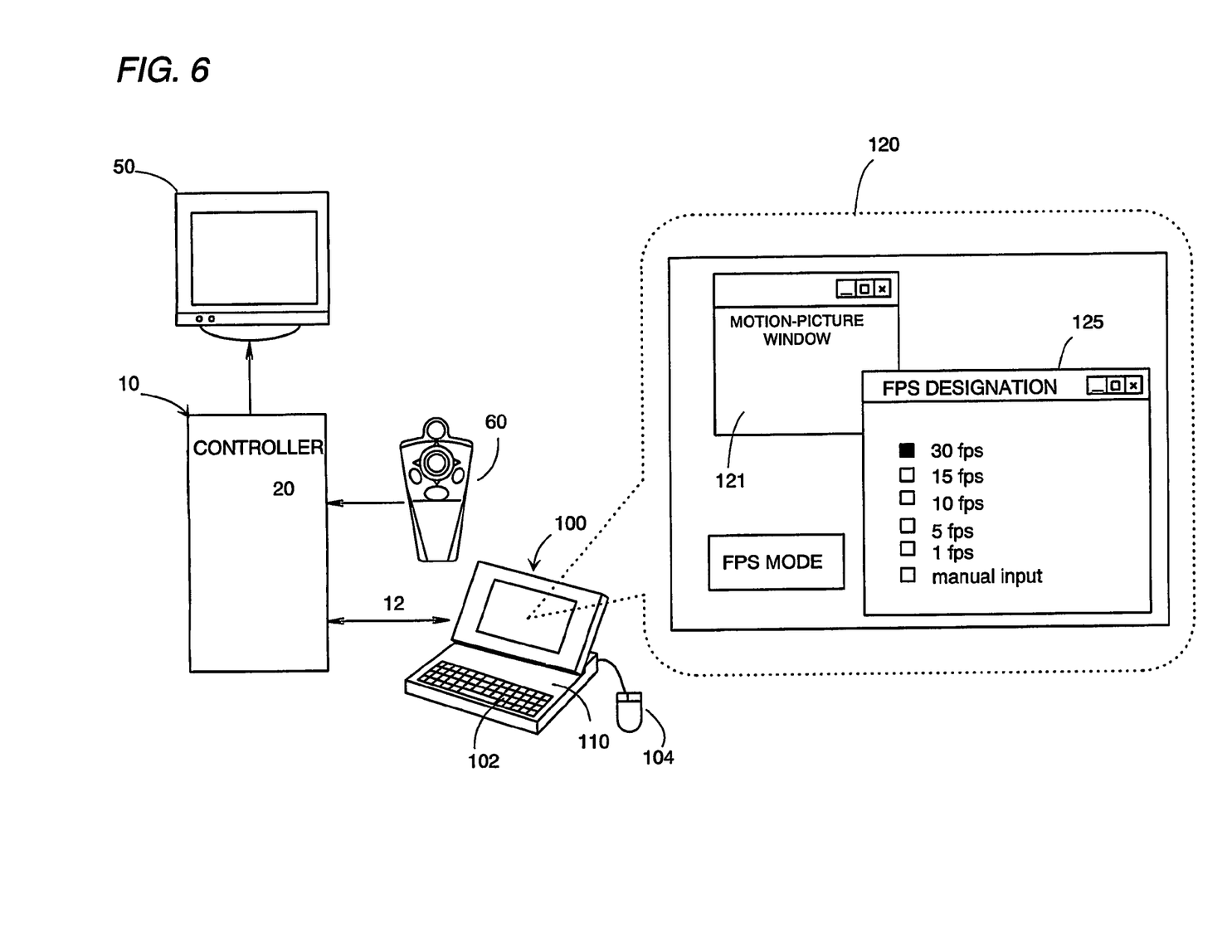

In addition, the menu on the second monitor 120 includes a window 125, as shown in FIG. 6, for designating the number of frames per second (fps) transmitted from the first controller 20 to the second controller 110. When this window 125 is selected from the menu, the second controller 110 comes into an fps mode permitting the operator to designate a desired one of predetermined fps values, 30 fps, 15 fps, 10 fps, 5 fps, and 1 fps, or to input a suitable fps value manually in consideration of the motion-picture image being transmitted at a default value of 30 fps and appearing in the motion-picture window. The designated fps value is sent to the first controller 20 which responds to transmit the motion-picture image at the designated fps value to the computer 100 for reproduction on the second monitor 120. Thus, the operator on the side of the computer 100 can suitably select the speed of the motion-picture image for balancing the speed and the traffic load in the communication link.

In this connection, the second controller 110 may be given a function to monitor a data transmission speed at which the motion-picture image is being transmitted from the master device, and to reduce the fps value as the data transmission speed lowers from a critical level by some reasons, thereby assuring a real-time image reproduction on the second monitor 120 but accompanied with somewhat jerky motion. The information about reduced fps value is also transmitted to the second controller 110 to be displayed on the second monitor for confirmation by the operator on the side of the computer 100. After the data transmission speed restores to a normal above the critical level, the first controller 20 responds to transmit the image at the default value of 30 fps.

Alternatively, the first controller 20 may be designed to make data compression of the motion-picture image as the data transmission speed being monitored by the computer lowers from a critical level. Thus, the current motion-picture image can be successfully reproduced on the side of the computer, assuring the determination of the inspection criteria on the side of the computer by referring to the current motion-picture image even when the data transmission speed is lowered. The data compression ratio is determined as a function of the data transmission speed, and the information of the compression ratio is transmitted to the second controller and displayed on the second monitor 120 for confirmation by the operator on the side of the computer 100. The data compression is made in accordance with a known lossy compression technique of eliminating suitable fractions of pixels of the motion-picture image in consideration of the transmission speed.

Figure 7:
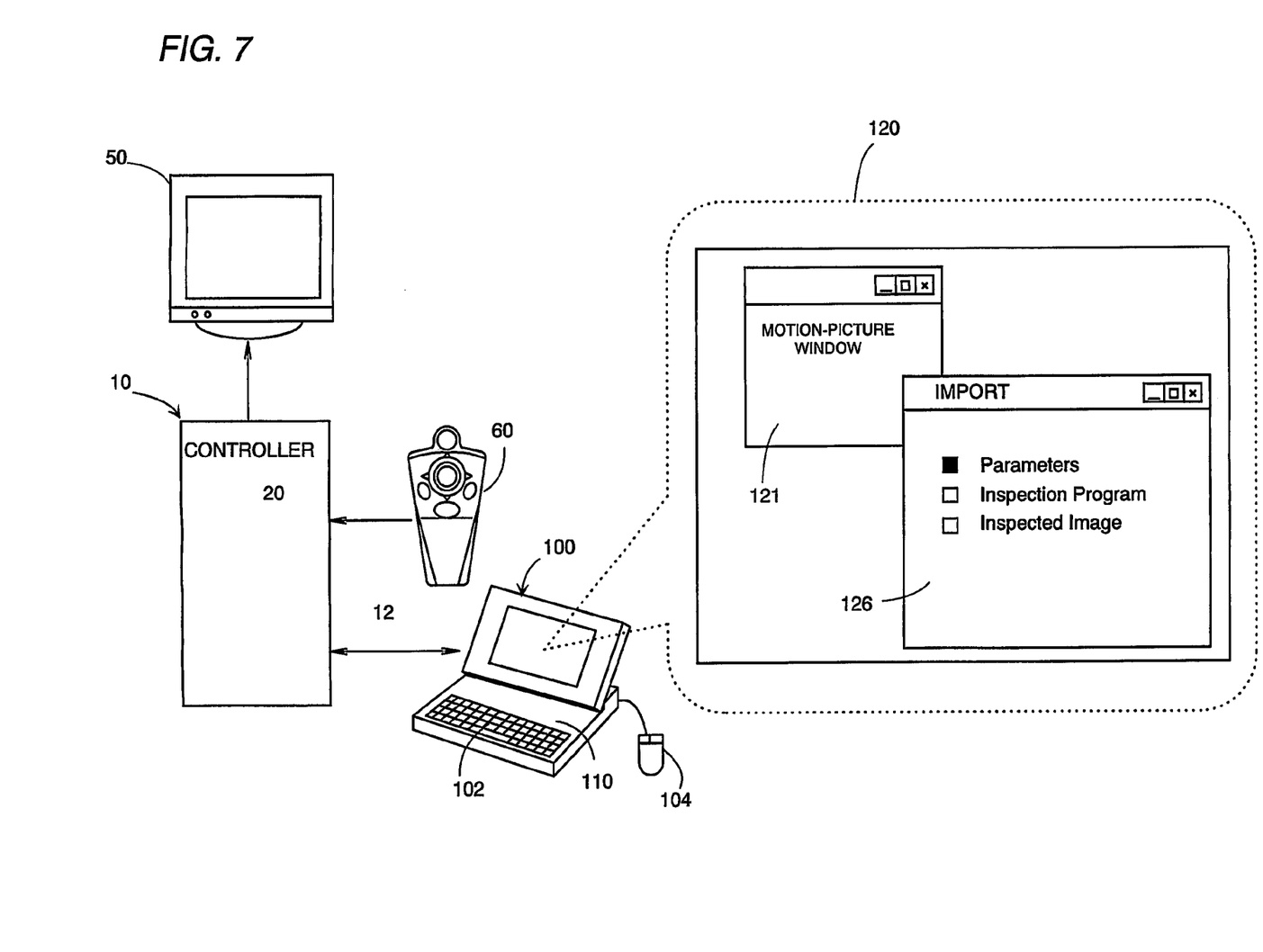
Figure 8:
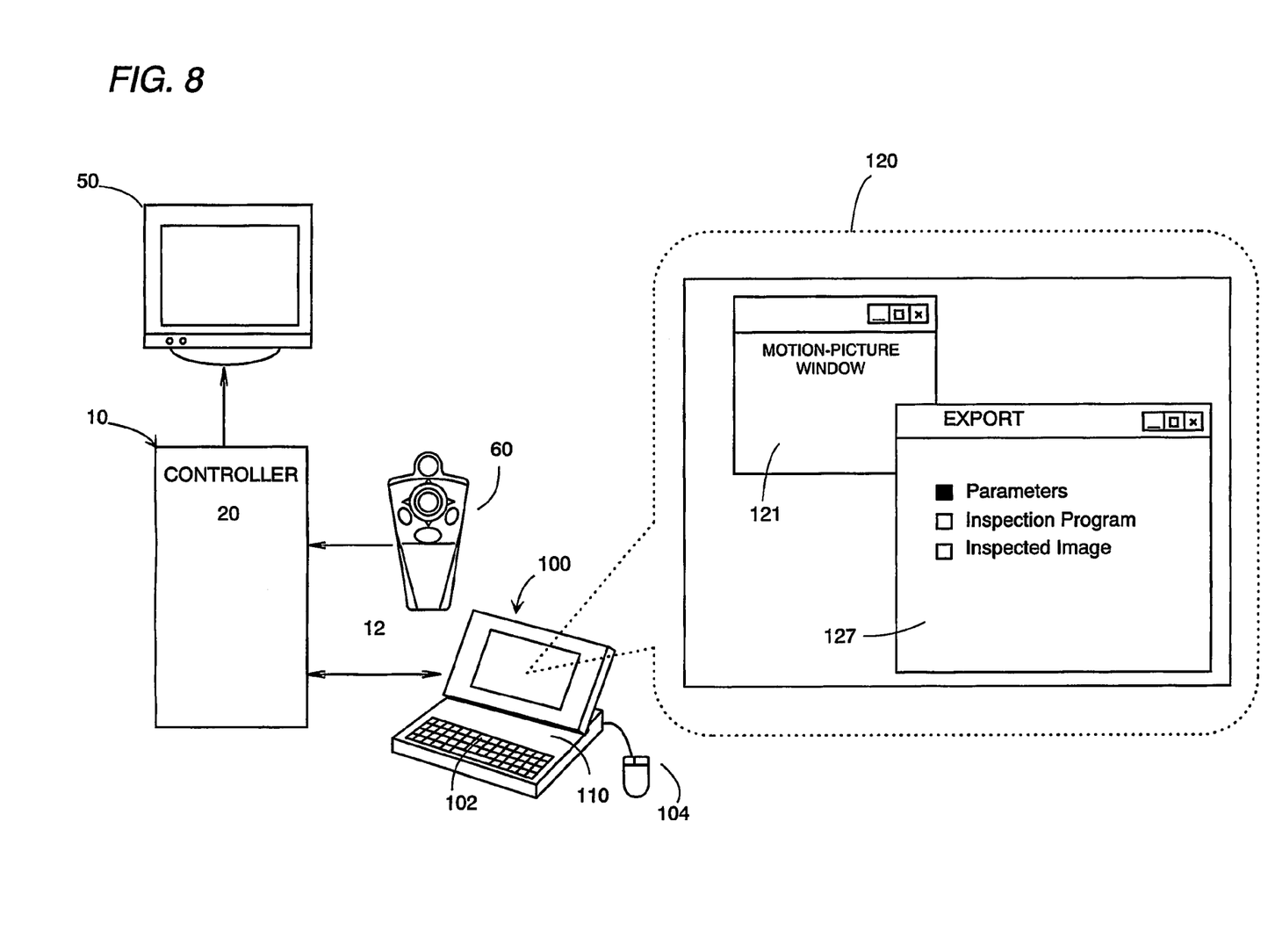

As shown in FIGS. 7 and 8, the second controller 110 is also designed to provide in the menu on the second monitor 120 import-export windows 127 and 128 which define an import-export mode for taking from the first controller 110 the parameters determining the inspection criteria and sending to the first controller the parameters entered on the side of the computer 100. For this purpose the second controller includes a memory (not shown) for storing the parameters taken from the memory 27 of the first controller 20 and those entered at the computer 100. Thus, the parameters can be edited on either side of the master device and the computer, which enhances operability of the system. Further, it is readily possible to modify the parameters on the side of the computer and returns the parameters back to the master device for another inspection of the object at the first controller in accordance with the modified criteria. As shown in these figures, the mode also enables the exchange of the inspection program and the inspected image, i.e., the still-picture image inspected with the inspection criteria. Check boxes are utilized for selection of which one or more of the parameters, the inspection program, and inspected image are exchanged. In this connection, the second controller is designed to give a programming mode for making or revising the inspection program on the side of the computer. Therefore, the inspection program can be easily drafted or modified on the side of the computer by taking an advantage of enhanced functions given to the computer. Further, with the capability of exchanging the inspected image, it is readily possible to try another inspection for the same image of the object in accordance with modified parameters and/or programs, making it easy to evaluate the effectiveness of the inspection criteria and the program and therefore alter the inspective criteria.

Figure 9:
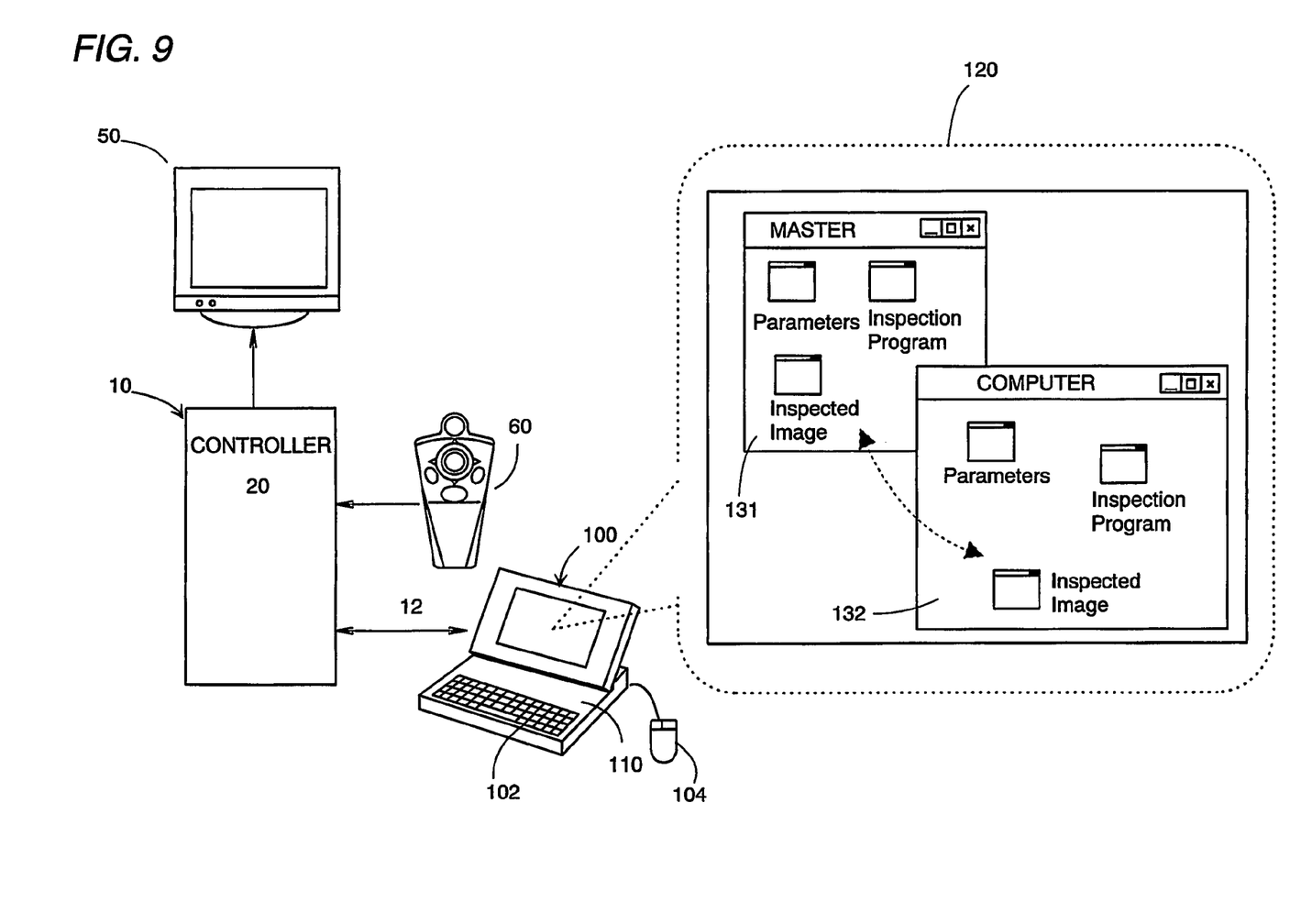

As shown in FIG. 9, the second controller is also programmed to provide windows 131 and 132 containing icons indicating files of parameters, the programs, and the inspected images respectively stored in the master device 10 and the computer 100. Thus, by taking the advantage of the GUI given to the computer, it is readily possible to exchange these files simply by using the mouse 104 to drag the file from one window to the other window.

Although the above embodiment is illustrated that the exchange of the parameters, the inspection programs, and the inspected image is made only by manipulation of the computer 100, it may be equally possible that the master device is also configured to make the same exchange for at least one of the parameters, the inspection program, and the inspected image at its own capability.

The invention claimed is:

1. An image processing and inspection system comprising:
a master device; and
a computer configured to intercommunicate with the master device,
said master device being adapted to be located adjacent to an object to be inspected and including: a video camera configured to take a motion-picture image as a sequence of still-picture images of the object; a first monitor; a first controller configured to display on said first monitor said motion-picture image as well as a menu prompting an entry of inspection criteria; and first input means for inputting said inspection criteria, said first controller being configured to process and inspect said still-picture images in accordance with the inspection criteria to give inspection results with regard to said object, and to transmit at least one of said still-picture images and said inspection results to said computer,
said computer being adapted to be disposed in a location remote from said master device and including: a second monitor; a second controller configured to display on said second monitor a menu prompting an entry of the inspection criteria, and to display said inspection results together with the still-picture images on said second monitor; and second input means for inputting said inspection criteria, said second controller being configured to transmit the inspection criteria input at said second input means to said first controller for inspection of the still-picture images at said first controller in accordance with the inspection criteria,
wherein said first controller is configured to transmit an instant motion-picture image to said computer, and said second controller is configured to display the instant motion-picture image on said second monitor.

2. The image processing and inspection system as set forth in claim 1, wherein
said first controller provides in the menu on said first monitor an operation mode of determining which one or both of said master device and said computer is responsible for giving the inspection criteria for the inspection of the object at said first controller, and
said second controller provides in the menu on said second monitor an operation mode of determining which one or both of said master device and said computer is responsible for giving the inspection criteria for the inspection of the object at said first controller.

3. The image processing and inspection system as set forth in claim 1, wherein
said first controller provides in the menu on said first monitor a display mode of determining which one or both of said first monitor and said second monitor is enabled, and
said second controller provides in the menu on said second monitor a display mode of determining which one or both of said first monitor and said second monitor is enabled.

4. The image processing and inspection system as set forth in claim 1, wherein
said second controller provides in the menu on said second monitor an fps mode of designating an fps value which is the number of frames being transferred of said motion-picture image being transferred per second from said master device to said computer, and
said second controller sends a designated fps value to the first controller such that said first controller responds to transfer the motion-picture image at the designated fps value to said computer.

5. The image processing and inspection system as set forth in claim 1, wherein
said second controller monitors a data transmission speed at which the motion-picture image is being transmitted from said master device, and sends the data transmission speed to said first controller, and
said first controller makes a data compression of said motion-picture image when said data transmission speed becomes lower than a critical level.

6. The image processing and inspection system as set forth in claim 5, wherein
said first controller makes a lossy compression to eliminate fractions of pixels of said motion-picture image for said data compression.

7. The image processing and inspection system as set forth in claim 1, wherein
said second controller monitors a data transmission speed at which said motion-picture image is being sent from said master device, and sends the data transmission speed to said first controller, and
said first controller reduces a number of frames of said motion-picture image transmitted per unit time when said transmission speed becomes lower than a critical level.

8. The image processing and inspection system as set forth in claim 1, wherein
said second controller provides in said menu on said second monitor a trim mode for cutting said motion-picture image into a segment of a desired size, and transmits to the first controller a trimming instruction with information of the size of the segment when the motion-picture image is cut into the segment, and
said first controller transmits the segmented motion-picture image to said computer in response to said trimming instruction.

9. The image processing and inspection system as set forth in claim 1, wherein
said second controller provides in the menu on said second monitor a parameter import-export mode for taking from said first controller parameters determining said inspection criteria utilized for the inspection carried out at said first controller, and sends to said first controller parameters entered at said computer for determination of the inspection criteria,
said second controller has a memory configured to store said parameters to be retrieved for modification of said parameter, and
said first controller has a memory configured to store said parameters for use to determine said inspection criteria.

10. The image processing and inspection system as set forth in claim 1, wherein
said first controller has a memory configured to store an inspection program describing a sequence of inspecting the object,
said second controller provides in the menu on said second monitor a programming mode for making the inspection program by utilizing said second input means and said second monitor,
said second controller has a memory configured to store the inspection program, and
said second controller provides in the menu on said second monitor a program import-export mode for taking said inspection program from the memory of said first controller for revising it at the computer as well as sending to said first controller said inspection program stored in the memory of said second controller for execution thereof at the first controller.

11. The image processing and inspection system as set forth in claim 1, wherein
said second controller has a memory configured to store said inspection results and an associated still-picture image transmitted from said master device, and
said second controller provides in said menu on said second monitor an export mode for transmitting to said first controller said associated still-picture image together with modified inspection criteria entered at said second input means so as to request another inspection of said associated still-picture image based upon the modified inspection criteria.

12. The image processing and inspection system as set forth in claim 1, wherein
said computer comprises a personal computer having a key board and a pointing device, and said second input means comprises the key board and the pointing device.

13. The image processing and inspection system as set forth in claim 2, wherein
said computer comprises a personal computer having a key board and a pointing device, and said second input means comprises the key board and the pointing device.

14. The image processing and inspection system as set forth in claim 3, wherein
said computer comprises a personal computer having a key board and a pointing device, and said second input means comprises the key board and the pointing device.

15. The image processing and inspection system as set forth in claim 4, wherein said computer comprises a personal computer having a key board and a pointing device, and said second input means comprises the key board and the pointing device.

16. The image processing and inspection system as set forth in claim 5, wherein said computer comprises a personal computer having a key board and a pointing device, and said second input means comprises the key board and the pointing device.

17. The image processing and inspection system as set forth in claim 6, wherein said computer comprises a personal computer having a key board and a pointing device, and said second input means comprises the key board and the pointing device.

18. The image processing and inspection system as set forth in claim 7, wherein said computer comprises a personal computer having a key board and a pointing device, and said second input means comprises the key board and the pointing device.

19. The image processing and inspection system as set forth in claim 8, wherein said computer comprises a personal computer having a key board and a pointing device, and said second input means comprises the key board and the pointing device.

20. The image processing and inspection system as set forth in claim 9, wherein said computer comprises a personal computer having a key board and a pointing device, and said second input means comprises the key board and the pointing device.

21. The image processing and inspection system as set forth in claim 10, wherein said computer comprises a personal computer having a key board and a pointing device, and said second input means comprises the key board and the pointing device.

22. The image processing and inspection system as set forth in claim 11, wherein said computer comprises a personal computer having a key board and a pointing device, and said second input means comprises the key board and the pointing device.

* * * * *